(12) United States Patent
Lu et al.

(10) Patent No.: US 10,487,112 B2
(45) Date of Patent: Nov. 26, 2019

(54) PEDIOCOCCUS ACIDILACTICI DERIVED ANTIMICROBIAL HEXAPEPTIDE AND PREPARATION METHOD THEREOF

(71) Applicant: Jiangnan University, Wuxi (CN)

(72) Inventors: Jian Lu, Wuxi (CN); Guolin Cai, Wuxi (CN); Juan Wang, Wuxi (CN); Dewei Zhu, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 15/746,596

(22) PCT Filed: Sep. 8, 2016

(86) PCT No.: PCT/CN2016/098420
§ 371 (c)(1),
(2) Date: Jan. 22, 2018

(87) PCT Pub. No.: WO2018/035892
PCT Pub. Date: Mar. 1, 2018

(65) Prior Publication Data
US 2019/0092811 A1 Mar. 28, 2019

(30) Foreign Application Priority Data
Aug. 25, 2016 (CN) .......................... 2016 1 0728511

(51) Int. Cl.
| | | |
|---|---|---|
| *A61K 38/08* | (2019.01) | |
| *A61K 38/00* | (2006.01) | |
| *C07K 7/06* | (2006.01) | |
| *C07K 7/00* | (2006.01) | |
| *A23K 20/147* | (2016.01) | |
| *A23K 20/195* | (2016.01) | |
| *A01N 37/18* | (2006.01) | |
| *B01D 15/32* | (2006.01) | |
| *B01D 15/34* | (2006.01) | |
| *B01D 15/36* | (2006.01) | |
| *B01D 61/14* | (2006.01) | |
| *B01D 61/58* | (2006.01) | |

(52) U.S. Cl.
CPC ................ *C07K 7/06* (2013.01); *A01N 37/18* (2013.01); *A23K 20/147* (2016.05); *A23K 20/195* (2016.05); *B01D 15/325* (2013.01); *B01D 15/34* (2013.01); *B01D 15/363* (2013.01); *B01D 61/145* (2013.01); *B01D 61/58* (2013.01); *A61K 38/00* (2013.01)

(58) Field of Classification Search
CPC .......... A61K 38/00; A61K 38/08; C07K 7/06; C07K 7/00
USPC ........... 530/300, 329; 514/1.1, 2.4, 2.8, 21.8
See application file for complete search history.

(56) References Cited

U.S. PATENT DOCUMENTS 7,163,797 B2 * 1/2007 Ruben .................... C07H 21/04
435/252.3
7,280,923 B2 * 10/2007 Woods, Jr. ........... G01N 23/207
702/27

OTHER PUBLICATIONS

Uni Prot B3H610, pp. 1-4. Integrated into UniProtKB/TrEMBL, Jul. 22, 2008.*
Damon et al, "Interaction network of antimicrobial peptides of Arabidopsis thaliana, based on high-throughput yeast two-hybrid screening," Plant Physiology and Biochemistry, 2012, 58: 245-252.*

* cited by examiner

*Primary Examiner* — Julie Ha
(74) *Attorney, Agent, or Firm* — IPro, PLLC

(57) ABSTRACT

A *Pediococcus acidilactici* derived antimicrobial hexapeptide and a preparation method thereof are disclosed herein. The antimicrobial peptide ENGEEE (SEQ ID NO: 1) is reported for the first time. Antimicrobial peptide lactein R16 has good pH stability and thermal stability, has an effect on inhibiting *Escherichia coli*, *Listeria monocytogenes* and *Staphylococcus aureus* and is capable of effectively reducing the amount of the *Escherichia coli* in soybean meal. Secondly, the antimicrobial peptide lactein R16 has a certain effect on proliferating *Saccharomyces cerevisiae* and *Lactobacillus plantarum* and has certain capability of clearing hydrogen peroxide, hydroxyl radicals, DPPH radicals and superoxide anions. The antimicrobial peptide lactein R16 can be used for biological control and can be used as a feed additive to play important roles in substituting antibiotics and solving the feed safety problem.

4 Claims, 4 Drawing Sheets
Specification includes a Sequence Listing.

PEDIOCOCCUS ACIDILACTICI DERIVED ANTIMICROBIAL HEXAPEPTIDE AND PREPARATION METHOD THEREOF

TECHNICAL FIELD

The disclosure herein relates to the field of a *Pediococcus acidilactici* derived antimicrobial hexapeptide and a preparation method thereof and belongs to the field of bioengineering.

BACKGROUND

At present, a subtherapeutic dose of antibiotics is used as a feed additive to be widely applied to a feed for livestock and poultry and plays an important role in promoting the growth of animals and preventing some diseases, however, people further know the side effects of the antibiotics along with the frequent occurrence of antibiotic misuse events. Antibiotic misuse not only can result in endogenous infection of the animals and generate drug-resistant strains, but also can lower the immunologic functions of livestock and poultry, and more seriously, the residual antibiotics in livestock and poultry products can flow into human bodies in different ways and generate harm to the human bodies.

EU regulatory commission decided that antibiotic growth promoters were forbidden in animal breeding since January 2006. Since December 2013, US FDA issued Veterinary Feed Directive in which licensed veterinarians were required to supervise the use of the antibiotics and preventive antibiotics were forbidden in feeds for livestock within three years since 2014 to reduce antibiotic drug resistance problems brought to consumers eating the livestock to the maximum extent. South Korea will also comprehensively forbid feed antibiotics in July 2018.

As the bacterial resistance to the antibiotics and the residue problems of the antibiotics become increasingly serious, the research and development of a green feed additive have become a worldwide research topic, and a large number of searches prove that a novel feed additive such as a Chinese herbal extract, a microbial preparation, an enzyme preparation, a prebiotic, an antimicrobial peptide and an acidifying agent can effectively reduce or substitute the feed antibiotics, wherein the antimicrobial peptide has the advantages of relatively good antimicrobial and immunoregulatory activity, no residues, no side effects, no drug resistance and no bad influences on the environment so as to become a potential effective substitute of the antibiotics.

SUMMARY

In order to solve the problem, lactein having an effect on inhibiting bacteria is separated from a fermentation liquid of lactic acid bacteria capable of inhibiting the growth of *Escherichia coli*, and preliminarily identified by using a liquid chromatography-mass spectrometry (LC-MS), the molecular weight of the lactein is 705.63 Da, the isoelectric point of the lactein is 3.58 and the amino acid sequence of the lactein is ENGEEE. The invention also confirms, by using a chemical synthesis method, that the lactein has an effect on inhibiting various gram-positive bacteria, and the lactein is named lactein R16.

The first aim of the invention is to provide an antimicrobial peptide which has the amino acid sequence: ENGEEE (shown as SEQ ID NO. 1) and is named lactein R16.

The antimicrobial peptide is separated from the fermentation liquid of the lactic acid bacteria capable of inhibiting the growth of *Escherichia coli*.

The second aim of the invention is to provide a nucleotide fragment for encoding the antimicrobial peptide.

The third aim of the invention is to provide a recombinant vector or a genetically engineered bacterium capable of expressing the antimicrobial peptide. For example, encoding genes of several (such as 20) antimicrobial peptides can be connected end to end, a thrombin digestion site is added between every two fragments of genes, the whole fragment of gene is connected with the vector to obtain the recombinant vector which is transformed into a host bacterium so as to be expressed. The antimicrobial peptide can be obtained by carrying out thrombin digestion on an expressed product.

In an implementation of the invention, the vector can be pPIC9K.

In an implementation of the invention, the host bacterium can be *Pichia pastoris* GS115.

The fourth aim of the invention is to provide a composition containing the antimicrobial peptide.

In an implementation of the invention, the composition is a feed additive, a feed and a biological preservative.

The fifth aim of the invention is to provide applications of the antimicrobial peptide, the nucleotide fragment for encoding the antimicrobial peptide, the recombinant vector capable of expressing the antimicrobial peptide or the genetically engineered bacterium capable of expressing the antimicrobial peptide.

In an implementation of the invention, the antimicrobial peptide is applied as the feed additive or the biological preservative.

The sixth aim of the invention is to provide a method for inhibiting bacteria by using the antimicrobial peptide.

In an implementation of the invention, the bacteria are gram-positive bacteria or gram-negative bacteria.

In an implementation of the invention, the bacteria include *Escherichia coli, Listeria monocytogenes, Staphylococcus aureus* and the like.

The invention also provides a preparation method of the antimicrobial peptide, and the method comprises the steps of carrying out crude extraction, by ultrafiltration, on a fermented supernatant obtained by fermenting *Pediococcus acidilactici*, then, carrying out separation by using an anion exchange chromatographic column Hitrap Q FF and a gel filtration chromatography Superdux Peptide 10/300GL, and finally, carrying out separation and purification by using a reversed-phase column Phenomenex Luna/C18 to obtain an antimicrobial hexapeptide.

In an implementation of the invention, ultrafiltration means that ultrafiltration (molecular weight cut-off is 3000 Da) and concentration is carried out to realize 8-10 times concentration to obtain a crude extract.

In an implementation of the invention, the preparation method specifically comprises the steps:

(1) carrying out ultrafiltration and crude extraction: carrying out ultrafiltration (molecular weight cut-off is 3000 Da) and concentration to realize 8-10 times concentration to obtain the crude extract;

(2) carrying out separation by using an anion exchange chromatographic column Hitrap Q FF: loading a sample of the crude extract on an Hitrap Q FF chromatographic column to carry out separation to obtain two eluting peaks, collecting an active peak L2 having an antimicrobial effect for *Escherichia coli*, and carrying out freeze drying after dialysis;

(3) carrying out separation by using a gel filtration chromatography Superdux Peptide 10/300GL: loading a sample of the eluting peak L2 of the anion exchange chromatography on a Superdux Peptide 10/300GL gel filtration chromatographic column to carry out separation to obtain two eluting peaks, collecting an active peak N2 having an antimicrobial effect for *Escherichia coli*, and carrying out freeze drying after dialysis; and (4) carrying out separation by using a reversed-phase $C_{18}$ column: dissolving the sample subjected to freeze drying in the previous step by using 5% acetonitrile (containing 0.1% TFA, the same below), eluting the sample by using 5-50% linear gradient increasing acetonitrile by a 5% acetonitrile-balanced Phenomenex Luna/$C_{18}$ column, collecting an active eluting peak II, and carrying out rotary evaporation and freeze drying to obtain a final product.

The antimicrobial peptide has the beneficial effects:
(1) Compared with a database such as an antimicrobial peptide database, the antimicrobial peptide ENGEEE disclosed by the invention is reported for the first time.
(2) Active peptide lactein R16 having an obvious resistance to the gram-positive bacteria is prepared by using technologies such as ultrafiltration and chromatography, the preparation process is simple, good in separation effect, mild in operation condition, rapid and efficient, the product is high in purity, and the purity of the product is identified by an MS to reach not less than 95%.
(3) The antimicrobial peptide lactein R16 obtained by the invention has good pH stability and thermal stability, the minimum inhibitory concentration for *Escherichia coli* and *Listeria monocytogenes* is 6.4 mg·mL$^{-1}$, and the minimum inhibitory concentration for *Staphylococcus aureus* is 3.4 mg·mL$^{-1}$.
(4) The antimicrobial peptide lactein R16 disclosed by the invention has a certain effect on proliferating *Saccharomyces cerevisiae* and *Lactobacillus plantarum* and has little influences on other probiotics.
(5) The antimicrobial peptide lactein R16 disclosed by the invention has certain capability of clearing hydrogen peroxide, hydroxyl radicals, DPPH·radicals and superoxide anions with the clearance rates being respectively 25.65%, 70.13%, 79.42% and 10.11%.
(6) The antimicrobial peptide lactein R16 disclosed by the invention can be used for biological control, is an effective supplement for an amino acid sequence measured lactein library and can be used as the feed additive to play important roles in substituting antibiotics and solving the feed safety problem.

DETAILED DESCRIPTION

Figure 1:
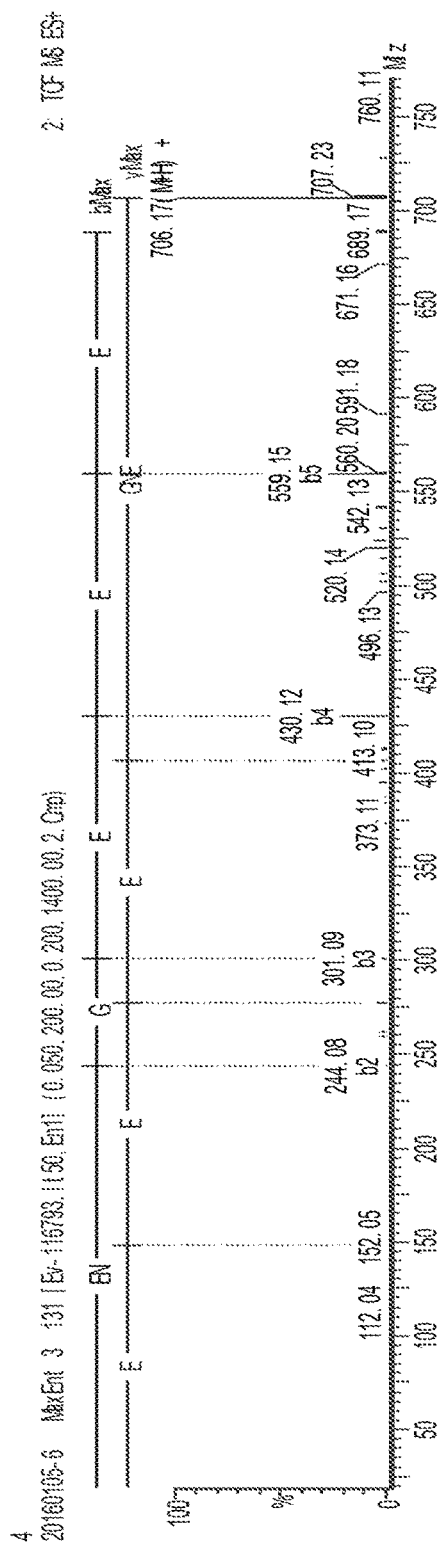
FIG. 1: mass spectrum identification chart.

Formulae of various buffer solutions in the invention can be found in a laboratory manual.

Embodiment 1: Preparation of Lactein R16

Antimicrobial hexapeptide lactein R16 is prepared by using the following method:

1. fermenting *Pediococcus acidilactici* to obtain the antimicrobial hexapeptide, and after centrifuging a fermented supernatant, collecting the supernatant, and carrying out ultrafiltration (the molecular weight cut-off is 3000 Da) and concentration to realize 8-10 times concentration to obtain a crude extract;

2. carrying out separation by using an anion exchange chromatography Hitrap Q FF: loading a sample of the crude extract on an Hitrap Q FF chromatographic column to carry out separation to obtain two eluting peaks, collecting an active peak having an antimicrobial effect for *Escherichia coli*, and carrying out freeze drying after sufficiently dialyzing the collected active peak L2 by using Mill-Q water;

3. carrying out separation by using a gel filtration chromatography Superdux Peptide 10/300GL: loading a sample of the eluting peak L2 of the anion exchange chromatography on a Superdux Peptide 10/300GL gel filtration chromatographic column to carry out separation to obtain two eluting peaks, collecting an active peak having an antimicrobial effect for *Escherichia coli*, and carrying out freeze drying after sufficiently dialyzing the collected active peak N2 by using Mill-Q water;

4. carrying out separation by using a reversed-phase $C_{18}$ column: dissolving the sample subjected to freeze drying in the previous step by using 5% acetonitrile (containing 0.1% TFA, the same below), eluting the sample by using 5-50% linear gradient increasing acetonitrile by a 5% acetonitrile-balanced $C_{18}$ column, collecting an active eluting peak H3, and carrying out rotary evaporation and freeze drying to obtain a final product; and 5. carrying out identification by using an LC-MS: after dissolving the sample having the antimicrobial activity and being subjected to freeze drying in the previous step by using Mill-Q water, and carrying out identification by using the LC-MS, wherein the flowing phases are A (the ratio of acetonitrile to water to formic acid is equal to 30:970:1 (V:V:V)) and B (the ratio of acetonitrile to water to formic acid is equal to 700:300:1 (V:V:V)); the eluting program lasts for 0-10 min and adopts 100% A and 0% B, or lasts for 20 min and adopts 70% A and 30% B, or lasts for 30 min and adopts 0% A and 100% B, or lasts for 35 min and adopts 100% A and 0% B; the flow rate is 1 mL/min; and the column temperature is 30° C. The mass spectrum conditions are as follows: the voltage of a capillary tube is 3.88 kV, the voltage of a cone is 20 V, the temperature of an ion source is 120° C., the desolvation temperature is 300° C., the flow rate is 1 mL/min, and the split ratio is 50:1; and analyzing a result by using software MassLynx4.1.

Identified by using a mass spectrum, the antimicrobial peptide has the molecular weight of 705.17 Da and the amino acid sequence of E-N-G-E-E-E (shown as SEQ ID NO. 1).

Compared with a database such as an antimicrobial peptide database, the antimicrobial peptide is not reported.

Embodiment 2: Biological Characteristics of Lactein R16

Stability of Lactein R16 in pH 10 parts of purified active substance lactein R16 with the concentration of 100 mg·mL$^{-1}$ is selected, the pH of the lactein R16 is respectively regulated to be 1.0-10.0 by using 1.0 mol·L$^{-1}$ NaOH and 1.0 mol·L$^{-1}$ HCl, the lactein R16 is treated in a 37° C. water bath kettle for 2 h, then, the pH of the lactein R16 is regulated to be 4.5, and an antimicrobial experiment is performed to observe the inhibition of the lactein R16 to *Escherichia coli*. The result is shown as FIG. 2.

Figure 2:
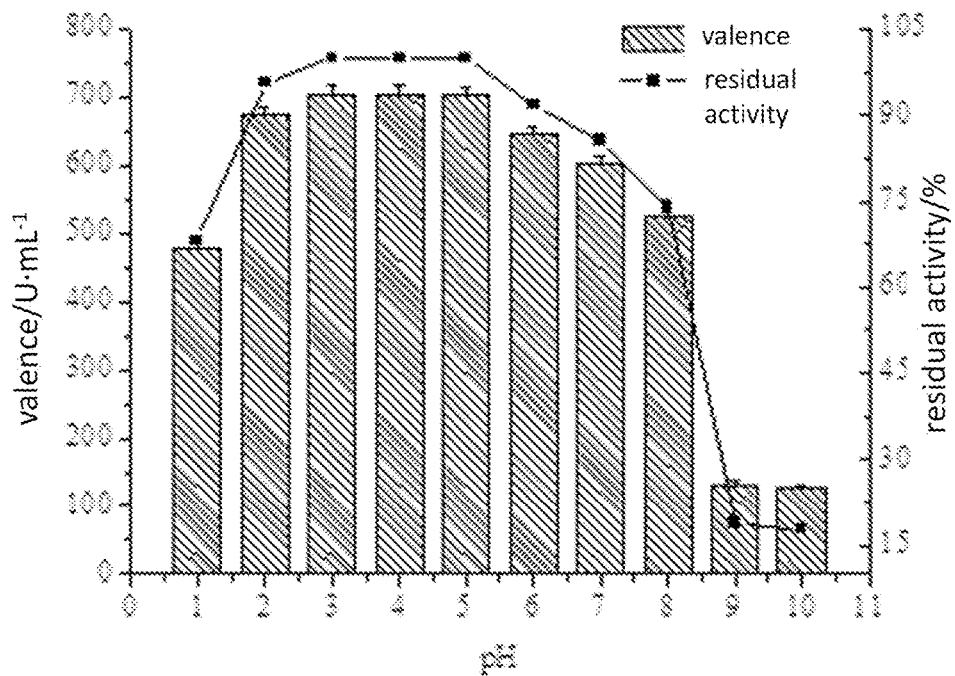
FIG. 2: influences of different pH values on lactein R16.

FIG. 2 shows that the antimicrobial activity of the lactein R16 reaches the maximum when the pH is 3.0-5.0. The antimicrobial activity of the lactein R16 is reduced step by step when the pH is 6.0-8.0, the reduction tendency is slow, and the residual activity is maintained at about 75%, which proves that the stability of the lactein R16 is reduced to a certain extent under such pH condition, but the pH has little influences on the stability of the lactein R16.

Thermal Stability of Lactein R16

8 parts of purified active substance lactein R16 with the concentration of 100 mg·mL$^{-1}$ is selected and is respectively treated at 40° C., 50° C., 60° C., 70° C., 80° C., 90° C. and 100° C. for 30 min and is subjected to high-pressure sterilization at 121° C. for 15 min, and an antimicrobial experiment is performed to observe the inhibition of the lactein R16 to *Escherichia coli*. The result is shown as FIG. 3.

Figure 3:
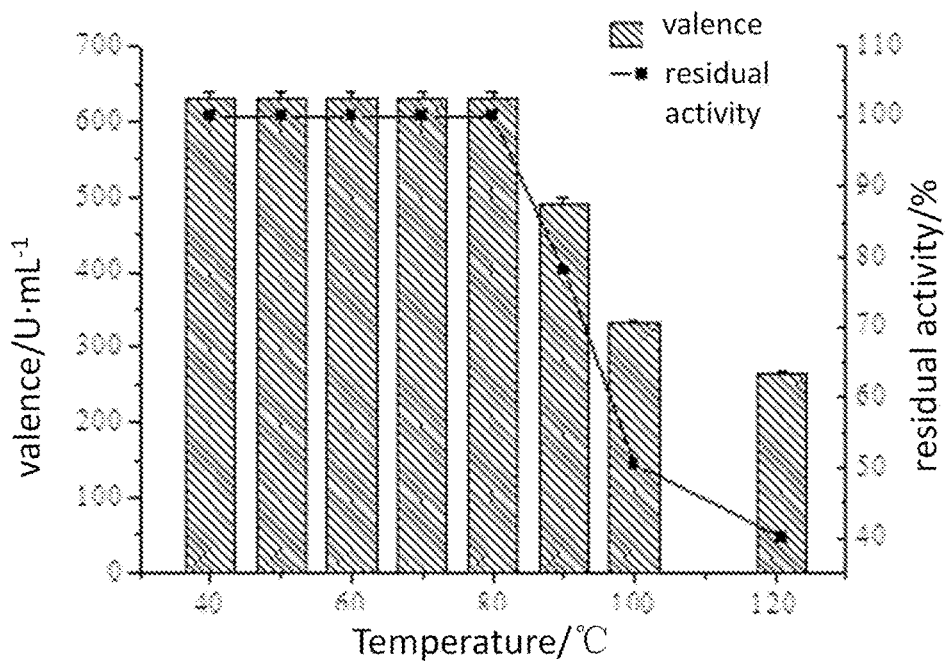
FIG. 3: influences of temperature on lactein R16.

It can be know from FIG. 3 that the lactein R16 has certain thermal stability, the antimicrobial activity of the lactein R16 has no obvious changes after the lactein R16 is treated at 40° C., 50° C., 60° C., 70° C. and 80° C. for 30 min, and the antimicrobial activity of the lactein R16 is only respectively lost by 21.95% and 49.47% after the lactein R16 is treated at 90° C. and 100° C. for 30 min. The antimicrobial activity of the lactein R16 is lost by 59.98% after the lactein R16 is treated at 121° C. for 15 min. The activity of the lactein R16 can be completely retained in the process of pelletizing at the temperature of 75-85° C. for 1-2 min.

Antimicrobial Spectrum of Lactein R16

8 parts of purified active substance lactein R16 with the concentration of 100 mg·mL$^{-1}$ is selected, and an inhibiting effect of the lactein R16 on *Escherichia coli*, *Listeria monocytogenes* and *Staphylococcus aureus* is detected by using an oxford-cup method.

Pathogenic microorganisms such as *Escherichia coli* and *Listeria monocytogenes* are easily carried in the transportation and storage processes of a feed and can enter bodies of animals along with the feed to induce intestinal infectious diseases of the animals and seriously threaten the health of the animals. The inhibiting effect of the lactein R16 on common pathogenic bacteria of the animals is shown as table 1.

TABLE 1

Antimicrobial Spectrum of Lactein R16

| Bacteria | Antimicrobial level |
| --- | --- |
| *Escherichia coli* K99 | ++ |
| *Escherichia coli* JM109 | ++ |
| *Escherichia coli* ATCC 25922 | + |
| *Listeria monocytogenes* CMCC(B)54002 | ++ |
| *Staphylococcus aureus* ATCC 6538 | +++ |

Note:
"+++" represents for strong inhibition, "++" represents for relatively strong inhibition, "+" represents for inhibition, and "−" represents for no inhibition.

It can be known from table 1 that the lactein R16 shows relatively strong antimicrobial activity for *Staphylococcus aureus*, *Escherichia coli* K99, *Escherichia coli* JM109 and *Listeria monocytogenes*, wherein the antimicrobial effect for *Staphylococcus aureus* is strongest.

Minimum Inhibitory Concentration of Lactein R16

The antimicrobial activity is detected by adopting a minimum inhibitory concentration (MIC) method, and the operation is as follows:

(a) inoculating the bacteria into an LB liquid culture medium according to the inoculation amount of 1%, and carrying out shaking culture over the night at 37° C. and 200r·min$^{-1}$;

(b) inoculating the culture solution into 20 mL of the LB liquid culture medium according to the inoculation amount of 1%, and carrying out shaking culture at 37° C. and 200r·min' until the OD$_{600}$ is equal to about 0.5;

(c) inoculating a bacterial suspension of which the OD$_{600}$ is equal to 0.5 into 10 mL of the LB liquid culture medium according to the inoculation amount of 0.01%, and carrying out vibration and uniform shaking to control the bacterial density at $1*10^5$-$5*10^5$ CFU·mL$^{-1}$, and measuring the MIC;

(d) carrying out gradient dilution on antimicrobial active substances to ensure that the final concentrations of the antimicrobial active substances are 256, 128, 64, 32, 16, 8, 4, 2 and 1 mg·mL$^{-1}$;

(e) adding 450 μL of the prepared bacterial suspension into an aseptic tissue culture plate, and then, respectively adding 50 μL of antimicrobial active substance diluents with corresponding concentrations to ensure that the concentrations of to-be-measured antimicrobial active substances are respectively 25.6, 12.8, 6.4, 3.2, 1.6, 0.8, 0.4, 0.2 and 0.1 mg·mL$^{-1}$; and carrying out culture in a 37° C. constant-temperature incubator for 18-24 h by taking 500 μL of the bacterial suspension as a positive control and 500 μL of the LB liquid culture medium as a negative control; and (f) observing whether bacteria are precipitated at the bottom of each hole or not, and determining that the minimum concentration at which no precipitated bacteria are visible to naked eyes is the MIC of the antimicrobial active substances.

The MICS of the lactein R16 to *Escherichia coli*, *Listeria monocytogenes* and *Staphylococcus aureus* are shown as table 2 from which it can be known that the MICS of the antimicrobial active substances to *Escherichia coli* and *Listeria monocytogenes* are 6.4 mg·mL$^{-1}$, and the MICs of the antimicrobial active substances to *Staphylococcus aureus* are 3.2 mg·mL$^{-1}$.

TABLE 2

MICs of Lactein R16 to Bacteria

| Bacteria | MIC/mg · mL$^{-1}$ |
| --- | --- |
| *Escherichia coli* K99 | 6.4 |
| *Staphylococcus aureus* ATCC 6538 | 3.2 |
| *Listeria monocytogenes* CMCC(B)54002 | 6.4 |

Influences of Lactein R16 on Probiotics

Each of probiotics is subjected to two-stage activation, is inoculated into an MRS culture medium containing 6.4 mg·mL$^{-1}$ of antimicrobial active substances according to the inoculation amount of 1% and is cultured at the constant temperature of 37° C. for 24 h in contrast with the probiotics inoculated into the MRS culture medium. Coated plate counting is performed by using a viable count method. The result is shown as FIG. 4.

Figure 4:
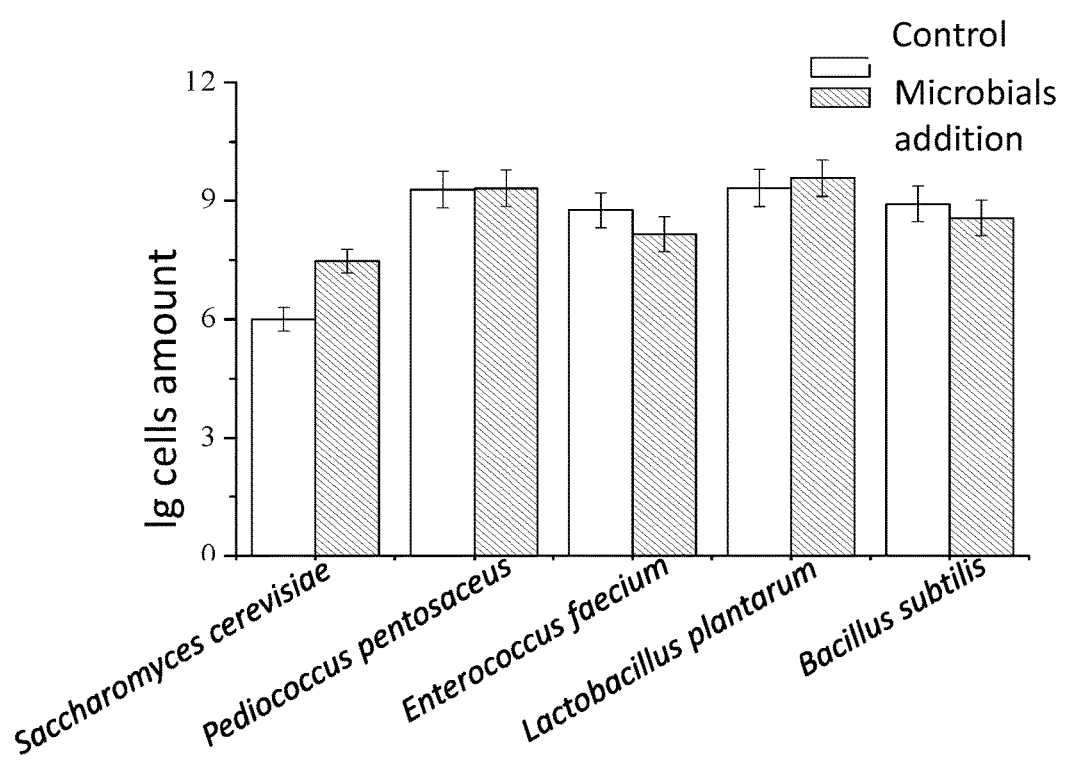
FIG. 4: influences of lactein R16 on growth of probiotics.

A microecological preparation used as one of green feed additives is widely applied to the feed, wherein a composite microecological preparation prepared from Saccharomycetes, Lactic Acid Bacteria and *Bacillus* is more common, not only can degrade and soften crude fibers and increase the content of proteins, but also can improve the palatability of the feed, regulate the intestinal microecological balance of the animals and promote digestive absorption and growth. *Saccharomyces cerevisiae*, *Pediococcus pentosaceus*, *Enterococcus faecium*, *Lactobacillus plantarum* and *Bacil-* lus subtilis are selected as a study object to study the influences of the lactein R16 on *Saccharomyces cerevisiae, Pediococcus pentosaceus, Enterococcus faecium, Lactobacillus plantarum* and *Bacillus subtilis*, and the result is shown as FIG. 4.

It can be known from FIG. 4 that the lactein R16 has a certain effect on proliferating *Saccharomyces cerevisiae* and *Lactobacillus plantarum*, wherein the effect on proliferating *Saccharomyces cerevisiae* is more obvious, and the amount of *Saccharomyces cerevisiae* is increased by 24.50% as comparison with that of a contrast. The lactein R16 has a certain effect on inhibiting *Enterococcus faecium* and *Bacillus subtilis*, but the inhibiting amplitude is relatively low, and the total bacterial counts of *Enterococcus faecium* and *Bacillus subtilis* are respectively reduced by 6.92% and 4.03% as comparison with that of the contrast and can reach about $10^8$ CFU·mL$^{-1}$ after *Enterococcus faecium* and *Bacillus subtilis* grow for 24 h. The total bacterial count of *Pediococcus pentosaceus* has no obvious changes as comparison with that of the contrast, which proves that the lactein R16 has no influences on *Pediococcus pentosaceus*.

Antioxidant Capability of Lactein R16

The feed contains a certain quantity of unsaturated fat, fatty acid, lipid-soluble vitamin, carotenoid and other lipid-soluble substances, which are easily oxidized in a storage process of the feed, and particularly fat and fatty acid can be oxidized to result in rancidity to generate different compounds such as aldehyde, alcohol, fat and acid which may generate various peculiar smells to seriously affect the palatability of the feed, and some compounds can generate adverse effects for the animals due to certain toxicity. The antioxidant capability of the lactein R16 to hydrogen peroxide, hydroxyl radicals, DPPH.radicals and superoxide anions is shown as FIG. 5.

Figure 5:
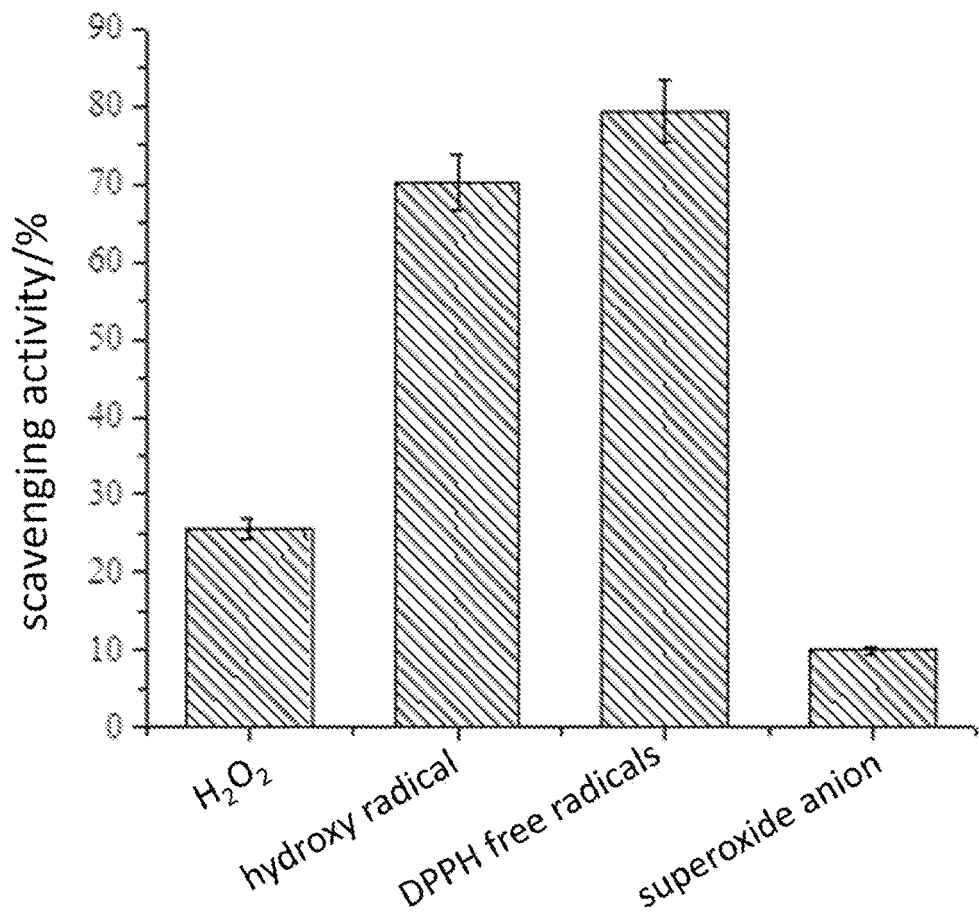
FIG. 5: clearing capability of antimicrobial active substances to hydroxyl radicals, DPPH radicals and superoxide anion radicals.

It can be know from FIG. 5 that the lactein R16 has certain capability of clearing hydrogen peroxide, hydroxyl radicals, DPPH.radicals and superoxide anions, wherein the capability of clearing the DPPH.radicals is highest, and the clearance rate reaches 79.42%; the capability of clearing the hydroxyl radicals is second highest, and the clearance rate is 70.13%, and the capabilities of clearing the superoxide anions and hydrogen peroxide are lowest, and the clearance rates are only 10.11% and 25.65%.

Embodiment 3: Application of Lactein R16

Application Method:

(a) crushing soybean meal by using a blade crusher, adding 4 parts (the weight of each part is 40 g) of soybean meal with the serial numbers of group 5, group 6, group 7 and group 8 into a 500 mL fermentation flask, and carrying out sterilization at 105° C. for 10 min;

(b) carrying out fermentation under conditions shown as table 3.

TABLE 3

Initial Fermentation Conditions of Soybean Meal Containing Lactein R16

| Fermentation Conditions | Parameter level | | | |
|---|---|---|---|---|
| | contrast | group 3 | contrast | group 4 |
| sample loading volume/g | 40 | 40 | 40 | 40 |
| Addition amount/g of antimicrobial active substances | 0 | 0.512 | 0 | 0.512 |
| Inoculation amount/mL of *Escherichia coli* with the concentration of $10^3$ CFU · mL$^{-1}$ | 1 | 1 | 1 | 1 |
| Material-to-liquid ratio | 1:0.8 | 1:0.8 | 1:0.12 | 1:0.12 |
| Fermentation temperature/° C. | 37 | 37 | 37 | 37 |
| Fermentation time/h | 48 | 48 | 48 | 48 |

(c) measuring the amount of *Escherichia coli* according to the natural standard for measuring *Escherichia coli* in the feed.

The inhibiting effect of the lactein R16 to *Escherichia coli* in the soybean meal is studied by adding *Escherichia coli* into the sterilized soybean meal. The result shows that the amount of *Escherichia coli* is increased from 1380·100 g$^{-1}$ before fermentation to $4*10^6$·100 g$^{-1}$ after fermentation when the lactein R16 is not added, and the amount of *Escherichia coli* is increased from 1380·100 g$^{-1}$ before fermentation to 123·100 g$^{-1}$ after the lactein R16 is added, which proves that the lactein R16 can be used for greatly removing *Escherichia coli* in the soybean meal while effectively reducing the amount of *Escherichia coli*, and the removal rate reaches 33.44%.

In consideration of a certain difference between industrial soybean meal fermentation realized by using lactic acid bacteria and laboratory fermentation, on the basis of original experiment, a soybean meal fermentation experiment is performed by changing the material-water ratio of 1:0.8 into 1:0.12 and keeping other experiment conditions unchanged, and the result shows that the removal rate of the lactein R16 to *Escherichia coli* in the soybean meal is increased from 33.44% to 56.64%, which proves that the lactein R16 can sufficiently act on *Escherichia coli* under an industrial condition.

Embodiment 4: Application of Lactein R16

As the unique bacteriocin allowed to be used in food preservation at present, the lactein can be added into foods such as milk and meat products to inhibit the growth of contaminating bacteria and prolong the shelf life.

What is claimed is:

1. A composition comprising an antimicrobial peptide consisting of the amino acid sequence of SEQ ID NO: 1, and a soybean meal.

2. The composition of claim 1, further comprising *Escherichia coli*.

3. A method of inhibiting bacterial infection in a subject, comprising administering the composition of claim 1 to the subject in need thereof.

4. The method of claim 3, wherein the bacterial infection is selected from the group consisting of *Escherichia coli, Listeria monocytogenes* and *Staphylococcus aureus*.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Protein translated from synthetic DNA

<400> SEQUENCE: 1

Glu Asn Gly Glu Glu Glu
1               5